United States Patent
Janssen

(10) Patent No.: US 10,311,696 B2
(45) Date of Patent: Jun. 4, 2019

(54) PATIENT MONITORING METHOD AND SYSTEM PROVIDING INCIDENT GROUPING OF ALARM EVENTS

(71) Applicant: General Electric Company, Schenectady, NY (US)

(72) Inventor: Brian D. Janssen, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/497,936

(22) Filed: Apr. 26, 2017

(65) Prior Publication Data

US 2018/0315285 A1    Nov. 1, 2018

(51) Int. Cl.
G08B 21/04 (2006.01)

(52) U.S. Cl.
CPC ............... *G08B 21/0453* (2013.01)

(58) Field of Classification Search
CPC .......... A61B 5/746; A61B 5/002; A61B 5/01; A61B 5/145; A61B 5/0022; A61B 5/0205; A61B 5/0816; A61B 5/0031; A61B 5/0245; A61B 5/02455; A61B 5/7275; A61B 5/7282; H04L 41/0631; G06F 9/542; G05B 2219/31437; G05B 2219/31438

See application file for complete search history.

(56) References Cited

U.S. PATENT DOCUMENTS

| | | | |
|---|---|---|---|
| 6,434,258 B2 | 8/2002 | Wiens | |
| 8,018,584 B1 | 9/2011 | Amir | |
| 8,139,945 B1 | 3/2012 | Amir et al. | |
| 8,310,364 B2 | 11/2012 | Derks et al. | |
| 8,514,071 B2 | 8/2013 | Derks et al. | |
| 8,620,682 B2 | 12/2013 | Bechtel et al. | |
| 8,633,806 B2 | 1/2014 | Amir | |
| 9,055,928 B2 | 6/2015 | McCombie et al. | |
| 9,219,984 B1 | 12/2015 | Amir | |
| 9,306,665 B1 | 4/2016 | Amir | |
| 9,341,700 B2 | 5/2016 | Amir et al. | |
| 2004/0098459 A1* | 5/2004 | Leukert-Knapp | G06F 11/327 709/206 |

(Continued)

OTHER PUBLICATIONS

Gorges, Mattias et al., "Improving Alarm Performance in the Medical Intensive Care Unit Using Delays and Clinical Context", International Anesthesia Research Society, vol. 108, No. 5, May 2009.

*Primary Examiner* — James J Yang
*Assistant Examiner* — Kevin Lau
(74) *Attorney, Agent, or Firm* — Andrus Intellectual Property Law, LLP

(57) ABSTRACT

A method of monitoring a patient includes recording physiological parameter data from the patient and detecting a first alarm event. A group alarm timer is activated based on an initiation time of the first alarm event, and one or more subsequent alarm events are detected while the group alarm timer is active. For each detected subsequent alarm event, a determination is made whether the respective subsequent alarm event is part of an incident group with the first alarm event. The group alarm timer is stopped at a termination time based on termination of all alarm events in the incident group. An incident group designator is generated identifying the incident group.

19 Claims, 7 Drawing Sheets

(56) References Cited

U.S. PATENT DOCUMENTS

| | | | |
|---|---|---|---|
| 2011/0199214 A1* | 8/2011 | Gawlick | A61B 5/0008 340/573.1 |
| 2014/0145848 A1 | 5/2014 | Amir | |
| 2014/0275818 A1* | 9/2014 | Kassem | A61B 5/746 600/301 |
| 2015/0065832 A1* | 3/2015 | Manion | A61B 5/746 600/340 |
| 2015/0067613 A1* | 3/2015 | Kim | G06F 3/017 715/863 |
| 2015/0195154 A1* | 7/2015 | Hevizi | H04L 43/024 706/50 |

* cited by examiner

PATIENT MONITORING METHOD AND SYSTEM PROVIDING INCIDENT GROUPING OF ALARM EVENTS

BACKGROUND

The present disclosure relates generally to medical devices and, more specifically, to medical monitoring devices for monitoring a patient's physiology and health status and for managing alarms based on the patient's physiology and health status, as well as technical alarms generated by medical monitoring and other devices and systems associated with patient care delivery.

In the field of medicine physicians often desire to continuously monitor multiple physiological characteristics of their patients. Oftentimes, such monitoring of multiple physiological characteristics involves the use of several monitoring devices simultaneously, such as a pulse oximeter, a blood pressure monitor, a heart monitor, a temperature monitor, etc. These monitoring devices may be separate devices or elements within a larger multifunction patient monitoring device. Additional monitoring, treatment, and/or support devices and systems may further be connected to or associated with the patient, such as for delivering fluids, medication, anesthesia, respiration assistance, patient requested assistance, lab/imaging results, EMR/EHR notifications/alerts, etc. or analyzing various patient-related data to determine and alert a clinician to a condition or patient state (e.g., sepsis protocols, APACHE scores, early warning scores). Each of these devices and systems may generate one or more alarms to alert a clinician of a problem, which may be a problem with the patient's physiology or health status, or may be a technical problem with the monitoring and/or care delivery device. Thus, at any given time one or more devices may be generating alarms requiring the attention of a clinician.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of monitoring a patient includes recording physiological parameter data from the patient and detecting a first alarm event. A group alarm timer is activated based on an initiation time of the first alarm event, and one or more subsequent alarm events are detected while the group alarm timer is active. For each detected subsequent alarm event, a determination is made whether the respective subsequent alarm event is part of an incident group with the first alarm event. The group alarm timer is stopped at a termination time based on termination of all alarm events in the incident group. An incident group designator is generated identifying the incident group.

One embodiment of a patient monitoring system includes one or more sensor devices that record physiological parameter data from a patient, a processor, and an incident analysis module executable on the processor. Specifically, the incident analysis module is executable to receive a first alarm event and a second alarm event, and to determine that the second alarm event is part of an incident group with the first alarm event. One or more subsequent alarm events are received while at least one of the first alarm event or the second alarm event is occurring, or within a predetermined time after termination of the first alarm event or the second alarm event. For each detected subsequent alarm event, the incident analysis module includes executable instructions to determine whether the respective subsequent alarm event is part of an incident group with the first alarm event. An incident group designator is generated identifying the incident group.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Currently available patient monitoring and alarm analytics assess alarm events as discreet events and do not assess their relation to one another. The present inventor has recognized that, in reality, groups of two or more alarms may occur within a time period that are so related to one another that they may be considered together as a single "incident." The present inventor further recognized that failure to account for the relations between alarm events and to group them accordingly provides incomplete or even inaccurate information regarding the progression of the patient's physiological condition and regarding the amount of care and resources utilized in treating the patient. Thus, current systems fail to provide context to the individual alarm events and their relationships with other events.

Upon recognition of the foregoing challenges and problems in the relevant art, the inventor developed the presently disclosed patient monitoring systems and methods that recognize when one or more alarm events are related and group them together as a single incident that can be analyzed as a whole and in context of the longitudinal view of all incidents and events in that time period. Thus, in addition to assessing the individual alarm events as provided in current systems, the alarm incident group can be assessed to provide further information and context, or "metadata," regarding the alarm events and the overall patient treatment requirements. Further, this generated "metadata" describing the event-driven incidents can be utilized to provide a longitudinal picture describing the relationships of alarm events occurring over a period of time and/or for multiple patients within a defined care environment. For example, a severity value of the incident group can be determined based on one or more of a duration of the incident group, a number of alarm events in the incident group, an alarm type and/or alarm level of the alarm events in the incident group, the number of clinicians and/or amount of clinician time spent tending to the incident group, other resources required in support of resolving the event(s), or the like.

Figure 1:
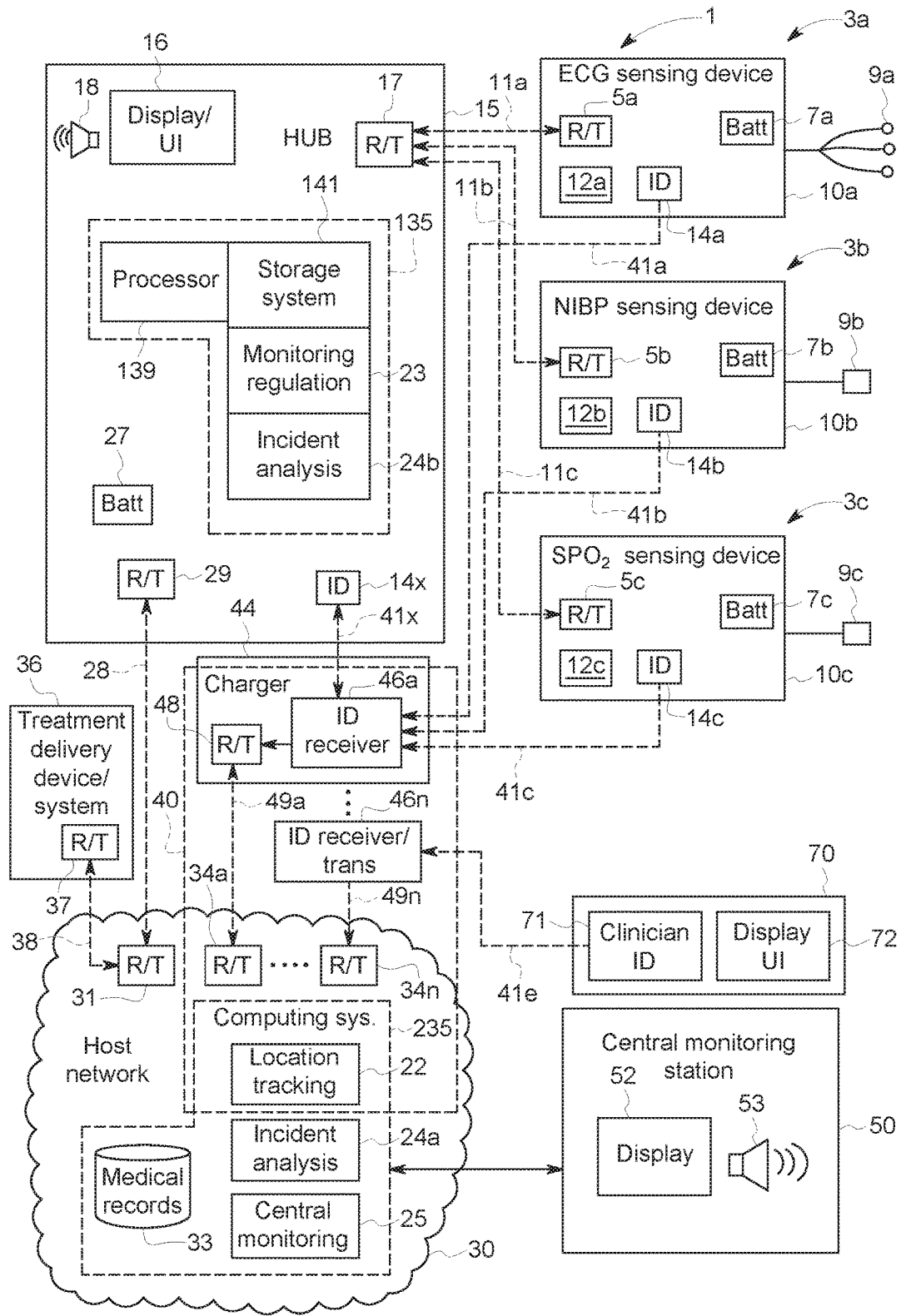
FIG. 1 is a schematic diagram of an exemplary patient monitoring system according to the present disclosure.

As exemplified in FIG. 1, a patient monitoring system 1 may be a wireless system including one or more wireless sensing devices (e.g., 3a-3c), each measuring different physiological parameter data from a patient. However, a person having ordinary skill in the art will understand that the wireless system is merely provided as an exemplary patient monitoring system, and that the disclosed system and method may utilize any type of patient monitoring system, whether connected to the patient via wired or wireless means. The sensing devices 3a-3c may be networked to a central hub or primary sensing device that determines a patient condition and regulates the various sensing devices in the network. In certain embodiments having a hub 15 (e.g., FIG. 1), the hub 15 may communicate with a central network for the medical care facility, e.g., host network 30. In another embodiment (which may or may not include a hub 15), the sensing devices 3a-3c may communicate directly with the host network 30, which may coordinate and/or regulate the operation of the various sensing devices. It will be understood by a person having ordinary skill in the art that the monitoring and control methods discussed herein as being executed by the hub 15 may equally be executed by a host network 30. There, the sensing devices may communicate with the host network 30 directly, or indirectly, through the hub. For example, the hub may serve as an amplifier and/or router for communication between the sensing devices and the host network 30. In such embodiments, each sensing device 3a-3c may process its own physiological parameter data and determine its own alarming conditions or such functions may be performed at the level of the host network 30. In other embodiments, the patient monitoring system 1 may include one or more traditional wired sensing devices providing wired connections between the hub or patient monitor and the sensors.

FIG. 1 depicts one embodiment of a patient monitoring system 1 containing three sensing devices 3a-3c in wireless communication with a hub 15. The hub 15 is in wireless communication with a host network 30 that contains medical records database 33. For example, the hub device 15 may be attached to the patient's body, placed on or near the patient's bed, or positioned within range of the patient, such as in the same room as the patient. The hub device 15 may be a separate stand alone device, or it may be incorporated and/or housed with another device within the system 1, such as housed with one of the sensing devices 3a-3c.

Each sensing devices 3a-3c contains one or more sensors 9a-9c for measuring physiological parameter data from a patient, and also includes a data acquisition device 10a-10c that receives the physiological parameter measurements from the sensors 9a-9c and transmits a parameter dataset based on those measurements to the hub device 15 via communication link 11a-11c. The sensors 9a-9c may be connected to the respective data acquisition device 10a-10c by wired or wireless means. The sensors 9a-9c may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, or the like. In the depicted embodiment, a first sensing device 3a is an ECG sensing device having sensors 9a that are ECG electrodes. A second sensing device 3b is a non-invasive blood pressure (NIBP) sensing device with a sensor 9b that is a blood pressure cuff including pressure sensors. A third sensing devices 3c is a peripheral oxygen saturation (SpO2) monitor having sensor 9c that is a pulse oximetry sensor, such as a standard pulse oximetry sensor configured for placement on a patient's fingertip. It should be understood that the patient monitoring system 1 of the present disclosure is not limited to the examples of sensing devices provided, but may be configured and employed to sense and monitor any physiological parameter of the patient. The examples provided herein are for the purposes of demonstrating the invention and should not be considered limiting.

The data acquisition device 10a-10c of each exemplary sensing devices 3a-3c may include an analog-to-digital (A/D) converter, which may be any device or logic set capable of digitizing analog physiological signals recorded by the associated sensor 9a-9c. For example, the A/D converter may be Analog Front End (AFE) devices. Each data acquisition device 10a-10c may further include a processing unit 12a-12c that receives the digital physiological data from the A/D converter and creates physiological parameter data for transmission to the hub device 15 and/or to the host network 30. Each data acquisition device 10a-10c may be configured differently depending on the type and function of sensing devices, and may be configured to perform various signal processing functions and/or sensor control functions. To provide just a few examples, the processing unit 12a in the ECG sensing device 3a may be configured to filter the digital signal from the ECG sensors 9a to remove artifact and/or to perform various calculations and determinations based on the recorded cardiac data, such as heart rate, QRS interval, ST segment/interval, or the like. The processing unit 12b in the NIBP monitor 3b may be configured, for example, to process the physiological data recorded by the sensors 9b in a blood pressure cuff to calculate systolic, diastolic, and mean blood pressure values for the patient. The processing unit 12c of the SpO2 sensing device 3c may be configured to determine a blood oxygenation value for the patient based on the digitized signal received from the pulse oximetry sensor 9c.

Accordingly, each processing unit 12a-12c may develop physiologic parameter data that, in addition to the recorded physiological data, also includes values measured and/or calculated from the recorded physiological data. The respective processing units 12a-12c may then control a receiver/transmitter 5a-5c in the relevant sensing devices 3a-3c to transmit the physiological parameter data to the hub device 15 via communication link 11a-11c. The physiological parameter data transmitted from the respective sensing devices 3a-3c may include the raw digitized physiological data, filtered digitized physiological data, and/or processed data indicating information about the respective physiological parameter measured from the patient. Additionally, one or more of the data acquisition devices 10a-10c may be configured to compare the physiological parameter data to one or more alarm thresholds to determine the presence of an alarm condition—i.e., detect an alarm event based on the physiological parameter data.

Upon detection of an alarm event by the respective sensing device 3a-3c, an alarm may be generated either by the sensing device 3a-3c (e.g., an auditory alarm via a speaker and/or visual alarm via a display) or the hub 15 (e.g., via speaker 18 and/or display 16), at a central monitoring station 50 (e.g., via speaker 53 and/or display 52), and/or a clinician device 70 (e.g., via a speaker and/or display 72). Notice of the alarm may be transmitted from the respective sensing device 3a-3c to the hub 15, or may be detected at the hub 15 in the first instance as explained above. Further, the system may be configured in various ways for a clinician to silence the respective alarm, which may be provided via the respective sensing device 3a-3c, at the hub 15, or at some other location, such as via the user interface 72 on the clinician device 70.

The alarm events may be triggered by analysis of the physiological parameter data, such as if alarm limits for the respective parameter data are exceeded (e.g., heart rate low), a parameter message alarm (e.g., apnea), or one or more particular data patterns are detected (e.g., indicating an arrhythmia such as tachy or asystole). Additionally, other alarm types may be generated, such as a technical alarm type or an alarm generated regarding treatment delivery to the patient. A technical alarm type is generated based on and/or as a result of a function of the sensing device 3a-3c, the hub 15, the treatment delivery device/system 36, or the like, and/or some component thereof. Examples of technical alarm types are low battery alerts, sensor off alerts (e.g., sensor(s) 9a-9c are not properly connected to the patient), sensor malfunction alerts (e.g., sensor(s) 9a-9c is not functioning properly), device malfunction alerts (e.g., sensing device 3a-3c or the treatment delivery device/system 36 is not functioning properly), data transmission malfunction alert (e.g., there is a problem with one or more communication links 11a-11c, 28, 38), or a technical problem regarding the function of a treatment delivery device/system 36 delivering therapy, medication, or the like to the patient.

In other embodiments, the processing units 12a-12c may not perform any signal processing tasks and may simply be configured to perform necessary control functions for the respective sensing devices 3a-3c. In such an embodiment, the parameter data set transmitted by the respective processing unit 12a-12c may simply be the digitized raw data or digitized filtered data from the various sensors 9a-9c, and all alarm event detection may occur at the hub 15 or at the host network 30.

Whether detected at each respective sensing device 3a-3c, at the hub 15, or by logic executed at the host network 30, the detected alarm events are received and analyzed by one or more incident analysis modules 24, or portions thereof (e.g., 24a or 24b), to determine whether each respective alarm event is part of an incident group 63. In various embodiments, the incident analysis module 24 may be stored and executed on the patient sensing device 3a-3c or one the hub 15 (e.g., 24a), and the resulting incident group information may be transmitted to a host network 30, such as the network where patient monitoring data and/or patient medical records are stored. In other embodiments, the incident analysis module 24 may be contained on and executed on a computing system of the host network 30 (e.g., 24b). In still other embodiments, the incident analysis module 24 may be divided between the patient monitoring device and the host network 30, where certain aspects of the incident group analysis are carried out at each location (i.e., the embodiment of FIG. 1 containing both 24a and 24b).

Figure 2:
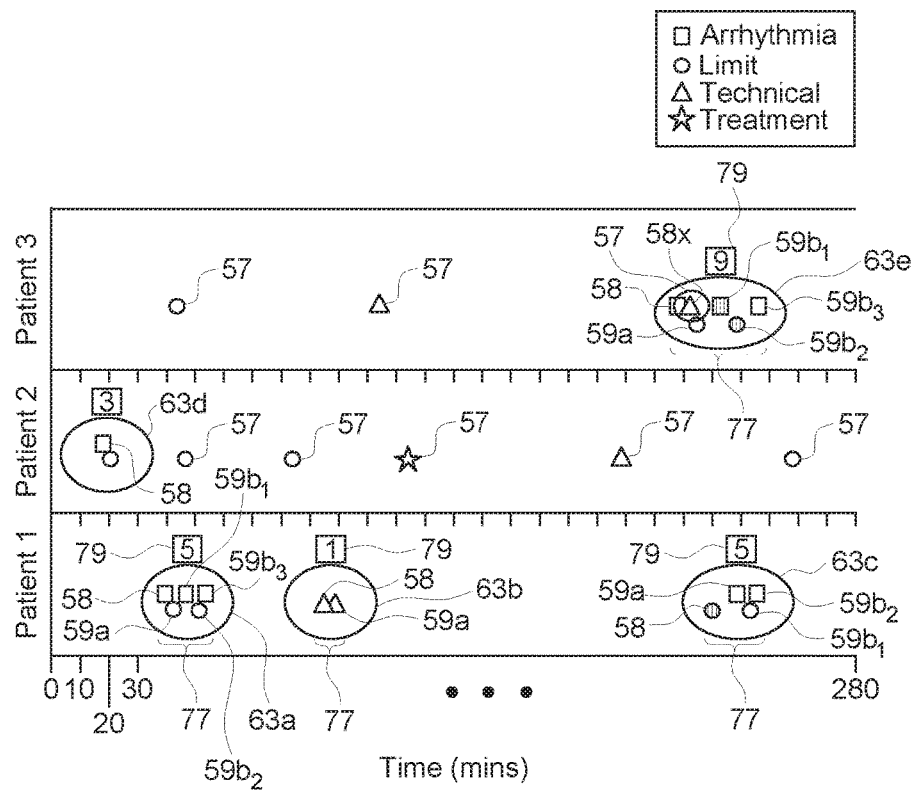
FIG. 2 is a diagram illustrating various alarm events occurring for three different patients over time.
Figure 3:
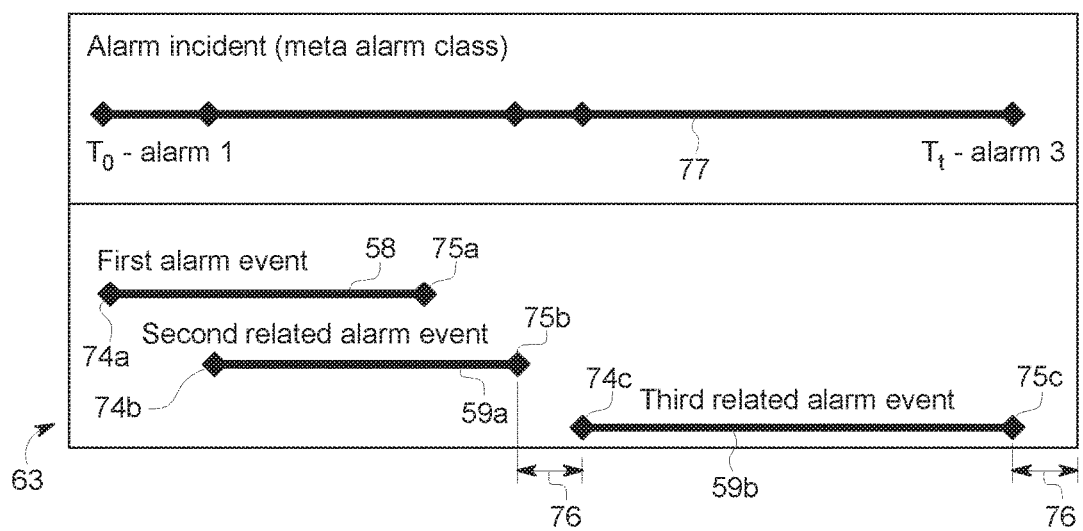
FIG. 3 is a time plot illustrating an exemplary incident group of alarm events, which are associated together over time in a meta alarm class.
Figure 4:
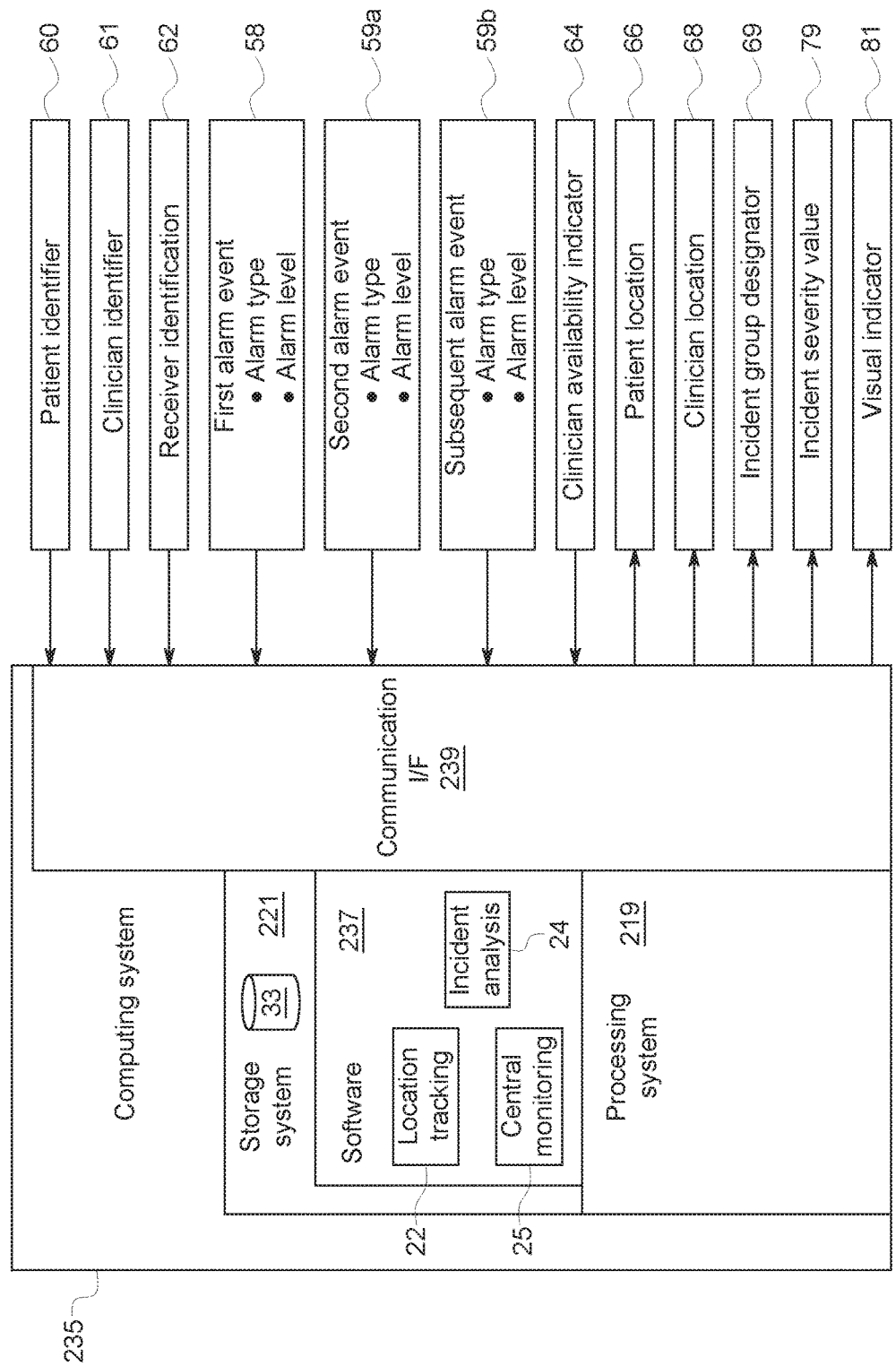
FIG. 4 is a schematic diagram of a computing system containing an incident analysis module as part of a patient monitoring system.

For example, the incident analysis module 24 may receive a first alarm event 58 and a second alarm event 59a, and then determine whether the second alarm event 59a is part of an incident group 63 with the first alarm event 58 (FIGS. 2-4). Each subsequent alarm event 59b is also assessed to determine whether it comprises part of the incident group 63. Various methods and steps for determining whether a second alarm event 59a and/or subsequent alarm event 59b are part of an incident group 63 with the first alarm event 58 are executed by the incident analysis module 24, which may be based on the time at which each alarm event occurs and/or the triggering basis (i.e., the event or reason upon which the respective alarm event was initiated).

FIG. 3, which is explained in more detail below, demonstrates this concept where multiple alarm events are grouped together in a meta alarm class, an incident group. The incident group may comprise any number of related alarm events that meet the predefined set of criterion and/or rules for grouping. As explained in more detail herein, these may include time-based criterion and/or alarm type criterion.

In certain embodiments, depending on the configuration setup, the system may pick and choose the types of alarm events that may be groupable together in an incident group. In such an embodiment, the determination of whether the second alarm events 59a and subsequent alarm events 59b are part of an incident group 63 with the first alarm event 58 is determined, at least in part, on the alarm type of the alarm event. For example, the incident analysis module 24 may be configured to disallow grouping alarm events of the technical alarm type with alarm events of the physiological alarm type based on the physiological parameter data—e.g., where the physiological parameter data exceeds one or more alarm thresholds. In many monitoring arrangements and applications, the technical alarm type alarm event is not generally going to be substantially related to such physiological alarm types. Further, in certain healthcare environments different clinicians or staff respond to technical alarm types as opposed to physiological alarm types. In certain embodiments, the incident analysis module 24 may include instructions executable to determine one or more permitted alarm types based on particular grouping rules applied to the alarm type of the first alarm event 58. For example, if the first alarm event is a technical alarm type, then the permitted alarm type for the incident group 63 may be confined to only technical alarm types. Similarly, if the first alarm event is a physiological alarm type, then the permitted alarm type may be only other physiological alarm types, or may be devised to allow multiple different alarm types but exclude technical alarm types (or other alarm types depending on the particular grouping rules).

Such alarm grouping can provide useful information regarding the patient's overall condition, as well as providing a basis for determining the amount of resources utilized to care for a patient. The usefulness of such incident grouping is highlighted and explained with respect to FIG. 2 where exemplary alarm events are depicted over time for three different patients. Analyzing each alarm event independently over the depicted period of time, patient 1 had eleven total alarm events, patient 2 had seven total alarm events, and patient 3 had eight total alarm events. Based on those numbers, it would appear that Patient 1 required significantly more clinician time and resources than Patient 2, for example, because Patient 1 had significantly more alarm events than Patient 2. However, if incident grouping analysis is conducted as disclosed herein, a different picture emerges.

In general, alarm events for a particular patient are divided into alarm incidents, which can either be comprised of just a single alarm event 57 or can be an incident group 63. An incident group 63 is comprised of two or more alarm events, including a first alarm event 58 and one or more subsequent alarm events 59. In the depicted example, Patient 1 had three separate alarm incidents, each being an incident group 63 of two or more distinct alarm events. Namely, a first incident group 63a was identified for Patient 1 consisting of 5 separate alarm events, a second incident group 63b was identified that includes two separate alarm events, and a third incident group 63c was identified to include four separate alarm events. Patient 2, on the other hand, had six distinct alarm incidents, with only one being an incident group 63 and the remaining five alarm incidents being single alarm events 57. The incident group 63*d* contains two distinct alarm events. Similarly, for Patient 3, the eight total alarm events are separable into four total alarm incidents, where the first two incidents each comprise a single alarm event 57, five of the alarm events are grouped into incident group 63*e*, and a single alarm event 57 alarm incident occurs during the incident group 63*e* based on a technical alarm event that, in this embodiment, could not be grouped together with alarm events in the incident group 63*e*.

Alarm events of four different exemplary, non-limiting, alarm types are represented in FIG. 2, including an arrhythmia alarm type (square designator), a limit alarm type (circle designator), a technical alarm type (triangle designator), and a treatment alarm type (star designator) generated by a treatment delivery device/system 36. The arrhythmia alarm type and limit alarm type are generally grouped herein as physiological alarm types, and in this example are permitted in the same incident group 63, whereas technical alarm types are considered separately and are not permitted in the same incident group 63 as the physiological alarm type. However, in other embodiments that may not be the case. The inclusion or exclusion of different alarm types (i.e., to which the application of a particular grouping methodology may be applied) is configurable pre, post, and during the data acquisition process through an alarm type selection process at the hub 15, or at some other location, such as via the user interface 72 on the clinician device 70 or monitoring station 50. For example, the grouping rules or methodology may be configurable via a selection interface on one of the above-listed devices allowing selection of the types of events and/or event sources that may be groupable, whether the grouping accounts for clinician location, whether the grouping allows for a predetermined time interval between overlapping events, or the like.

In certain embodiments, the system 1 may include one or more treatment delivery devices/systems 36 in communication with one or more of the host network 30 and/or the patient monitoring device, such as with the hub 15. A treatment delivery device/system 36 delivers treatment to the patient, such as medication or respiration therapy. Non-limiting examples of treatment delivery devices/systems 36 include anesthesia delivery devices, infusion pumps of various sorts, ventilators, respirators, blood glucose monitors, CO2 monitors, cardiac output monitors, etc.

The treatment delivery device(s)/system(s) 36 and patient monitoring device(s) 3*a*-3*c*, 15 are described herein for purposes of providing an explanatory example and are not limiting. Further, though the treatment delivery devices/systems 36 and patient monitoring devices 3*a*-3*c*, 15 are shown as communicating directly with the host network 30 (e.g., with receiver/transmitter 31), a person having ordinary skill in the art will understand in light of this disclosure that one or more of these systems may indirectly communicate with the host network 30, such as via an aggregation system or other middleware solutions. To provide just one example, communications from the patient monitoring devices 3*a*-3*c*, 15 may be provided through an alarm management system, such as an alarm management system provided by Ascom Holding AG. In other embodiments, additional alarm/alert generating systems (e.g., an EMR/EHR or an application analyzing various patient-related data to determine a condition or patient state such as a sepsis protocols, APACHE scores, or early warning scores) may interface with and transmit alert/alarm information to hub 15, the host network 30, or an alarm management system and be inputs to the incident analysis module 24.

The treatment delivery device/system 36 may generate its own alarms to alert a clinician to a problem with treatment delivery, which are referred to herein as treatment alarm type alarm events. For example, the treatment alarm type generated by the treatment delivery device/system 36 could include issues relating to an inability to deliver the prescribed treatment (e.g., insufficient anesthesia medication, an issue with an intravenous line, a leak in a respirator, a blockage of an airway). Upon detection of a treatment alarm type alarm event, the treatment delivery device/system 36 may transmit the alarm event to the host network 30 and/or to the hub 15. In the exemplary embodiment of FIG. 1, the treatment delivery device/system 36 has a receiver/transmitter 37 in communication with the receiver/transmitter 31 of the host network, which may be by any wireless protocol, examples of which are described herein. The treatment alarm type may be treated separately from the physiological alarm types (e.g., arrhythmia and limit alarm types) or they may be groupable with the physiological alarm types into a single incident group 63. Whether the system is configured to group treatment alarm types with physiological alarm types may depend on the workflow and setup of a particular healthcare location, or even a unit within a healthcare location, such as whether treatment alarm types are responded to by different clinicians than physiological alarm types.

With reference to the example of Patient 1, incident group 63*a* is comprised of three arrhythmia alarm types and two limit alarm types, which are considered related based on the fact that they overlapped one another in time such that each subsequent alarm event began while the previous alarm event was still occurring. Thus, each of the alarm events in incident group 63*a* overlap at least one other alarm event in the group. Specifically, the first arrhythmia alarm event is identified as a first alarm event 58 in the incident group 63*a*. The permitted alarm types for the incident group 63*a* are then defined based on the arrhythmia alarm event, which in the depicted embodiment includes arrhythmia alarm types and limit alarm types (both physiological alarm types). The second alarm event 59*a* is a limit alarm event and it overlaps in time with the first alarm event 58. Then, three subsequent alarm events 59*b* occur after the second alarm event 59*a*. Arrhythmia alarm event 59$b_1$ initiates after the first alarm 58 has ended but during the pendency of the second alarm 59*a*. The limit alarm event 59$b_2$ occurs after the second alarm event 59*a* has ended but before the end of the arrhythmia alarm event 59$b_2$. Another arrhythmia alarm event 59$b_3$ then initiates before the end of the limit alarm event 59$b_2$. The incident group 63*a* terminates after the last arrhythmia alarm event 59$b_3$ because no subsequent alarm event occurs during the pendency of that alarm event 59$b_3$ to continue the incident.

Incident group 63*b* is comprised of two technical alarm type alarm events which overlap in time. However, incident group 63*c* for Patient 1 is comprised of four distinct alarm events, three of which have some overlap in time and one (the first alarm event 58 in the incident group 63*c*) is separated from the group and ends prior to the start of the second alarm event 59*a*, which is an arrhythmia alarm type. In certain embodiments described in more detail below, the incident analysis module 24 may be configured to hold the incident group open for a period of time after a last occurring or persisting alarm event in a group in order to continue detecting alarm events for that additional period that may be incorporated in the same incident group 63.

In embodiments where technical alarm types are not grouped together in the same incident group with physiological alarm types, the occurrence of a subsequent alarm that is determined not to be part of an incident group is treated as a new first alarm event. The new first alarm event can trigger a second incident group analysis that may run in parallel and overlap in time with the first incident group analysis. In FIG. 2, for example, incident group 63e is comprised of five physiological alarm type alarm events. However, during the time period of the incident group 63e, a technical alarm type alarm event 58x occurs. The technical alarm type alarm event is not incorporated or included in the incident group 63e, and thus is treated as a first alarm event 58x. Should another technical alarm type alarm event occur in proximity to the technical alarm type first alarm event 58x, a new incident group would be formed by the two technical type alarm events. Such a configuration separating technical alarm events from physiological alarm events may be especially useful in environments where different clinicians or staff respond to technical alarm events versus physiological alarm events. In such a situation, it may be important to separately highlight and enumerate technical alarm events and physiological alarm events, even if they occur simultaneously, because each will require a response by a separate clinician and thus utilize different resources from one another.

In certain embodiments, alarm events occurring within a predetermined time interval following conclusion of an alarm event may be considered as part of the same incident group 63. This is illustrated in the example of FIG. 3, which graphically depicts an exemplary incident group 63 comprised of three related alarm events. Each alarm event has an initiation time 74 and termination time 75. The first alarm event 58 starts at an initiation time 74a and concludes at a termination time 75a. The second alarm event 59a starts at an initiation time 74b and concludes at a termination time 75b. The initiation time 74b of the second alarm event 59a occurs prior to the termination time 75a of the first alarm event 58, and thus the second alarm event 59a is determined to be part of the incident group 63 with the first alarm event 58. A third alarm event, subsequent alarm event 59c, occurs after the termination time 75b of the second alarm event 59a. However, in the depicted embodiment a time interval 76 is set whereby the incident analysis module 24 leaves an incident group open for a predetermined time following the last-occurring alarm event in the group such that if another alarm event is initiated within the predetermined time interval following conclusion of the last-occurring alarm event, then the subsequent alarm event initiated within the predetermined time interval 76 is be considered as part of the same incident group 63 as the prior alarm events. Here, the third and subsequent alarm event 59c has an initiation time 74c that is within the predetermined time interval 76 following the termination time 75b of the second alarm event 59a. Accordingly, the subsequent alarm event 59c is included in the incident group 63. Since no subsequent alarm event occurs during the pendency of the third related alarm event, nor during the time interval 76 following the termination time 75c of the third related alarm event (subsequent alarm event 59c) the incident group 63 is terminated. In various embodiments, the predetermined time interval 76 may be an adjustable value, such as adjustable by a system administrator and/or by a clinician. In this way, the predetermined time interval 76 may be adjusted to account for the realities of a given situation.

A duration 77 is determined for each alarm incident 57, 63. The continuous top bar of FIG. 3 depicts the duration 77 of the incident group 63. The initiation time $T_0$ of the incident group is taken as the initiation time 74a of the first alarm event 58. The termination time $T_t$ is designated as the termination time 75c of the last alarm event in the incident group 63. In other embodiments, the termination time $T_t$ may be determined based on additional logic. For example, the termination time $T_t$ may be at the conclusion of the time interval 76 following the latest occurring alarm event in the incident group 63. In other embodiments, the termination time may be further based on clinician location. As explained in more detail below, an incident group determination may be made based on whether a clinician remains present or continues to attend to the patient as a result of grouped alarm events. This may be determined, for example, based on a clinician location 66 determination provided by a location tracking system 40. In such an embodiment, the termination time may extend for as long as the clinician location 66 indicates that the clinician is still attending to the patient due to a previous alarm event, and such a determination of termination time may be extended for a predetermined time interval following the clinician's exit of the patient location 68. For a single alarm event 57, the duration may simply be determined as the time between the initiation time and termination time of the alarm event comprising that incident.

The termination time 75 of each alarm event 58, 59a, 59b may be the time when the alarm event was silenced, such as by a clinician providing input at a user interface to silence the alarm. Alternatively, the termination time 75 of a respective alarm event 58, 59 may be when the triggering basis for the respective alarm event 58, 59 is resolved or no longer present. For example, if the respective alarm event 58, 59 is a technical alarm event, elimination of the triggering basis is when the technical issue has been resolved (e.g., the battery has been replaced, the sensor has been placed back on the patient, etc.). Similarly, for a physiological alarm type, resolution of the triggering basis may be when the physiological parameter data no longer exceeds the relevant alarm limit. In certain embodiments, termination of an alarm event 58, 59 may be determined differently for different alarm types.

In certain embodiments, a group alarm timer may be activated at the initiation time $T_0$ of the group alarm event. The group alarm timer may continue while any alarm event in the incident group 63 is still active, and may be continued for the predetermined time interval 76 following the termination time 75 of the last remaining active alarm events in the incident group 63. The group alarm timer is then stopped at the termination time $T_t$ based on the termination of all alarm events or after the predetermined time interval 76 following termination of all alarm events in the incident group 63. In such embodiments, the recorded time between the initiation time and the termination time of the group alarm timer can be used to determine the duration 77 of each respective incident group 63.

After identifying an incident group 63, the incident analysis module 24 generates an incident group designator 69 identifying the incident group, such as identifying the alarm events 58, 59a, 59b in the incident group 63 and/or the initiation time $T_0$ and/or termination time $T_t$ of the incident group 63. In certain embodiments, the incident analysis module 24 may generate the incident group designator 69 after conclusion of the respective incident group 63. In other embodiments, the incident analysis module 24 may generate the incident group designator 69 piecewise in real time as the various aspects of the incident group 63 unfold. In certain embodiments, the incident group designator 69 may include additional information about the incident group 63, such as information regarding the alarm types or alarm levels therein, or even the incident severity value 79.

Referring again to FIG. 1, the receiver/transmitter 5a-5c of each sensing devices 3a-3c communicates via the respective communication link 11a-11c with the receiver/transmitter 17 of the hub device 15, which may include separate receiving and transmitting devices or may include an integrated device providing both functions, such as a transceiver. The receiver/transmitters 5a-5c of the sensing devices 3a-3c and the receiver/transmitter 17 of the hub device 15 may be any radio frequency devices known in the art for wirelessly transmitting data between two points. In one embodiment, the receiver/transmitters 5a-5c and 17 may be body area network (BAN) devices, such as medical body area network (MBAN) devices, that operate as a wireless network. For example, the sensing devices 3a-3c may be wearable or portable computing devices in communication with a hub device 15 positioned in proximity of the patient. Other examples of radio protocols that could be used for this purpose include, but are not limited to, Bluetooth, Bluetooth Low Energy (BLE), ANT, and ZigBee.

In various embodiments, one or all of the sensing devices 3a-3c may be equipped with a patient identification transmitter 14a-14c that emits a patient identifier 61 that is detected by a location tracking system 40. The location tracking system 40 receives the patient identifier 61 in order to determine the patient's location. Likewise, each clinician may also be equipped with a clinician identification transmitter 71 that emits a clinician identifier 60 detected by the location tracking system 40. The location tracking system 40 may be, for example, a real-time location system (RTLS) that provides immediate or real time tracking of the patients' locations, the clinicians' locations, and also the locations of various other individuals and/or devices within a healthcare facility or area. In the embodiment of FIG. 1, each sensing device 3a-3c includes a patient identification transmitter 14a-14c that transmits a patient identifier 61 associated with the patient. Since the sensing devices 3a-3c are body-worn devices, the patient identification transmitter(s) 14 can be used to determine a patient location within the care facility.

The hub 15 may also include a patient identification transmitter 14x that transmits a location of the hub 15. Such patient identification transmitter 14x in the hub 15 may be in lieu of or in addition to the identification transmitters 14a-14c in the sensing devices. In embodiments where the hub 15 is a small, body-worn device that is attached to the patient, the patient identification transmitter 14x in the hub 15 may be sufficient for patient location tracking purposes. In embodiments where the hub 15 is not a body-worn device, the patient identification transmitter 14x may be unreliable, by itself, for patient location tracking. In such embodiments, the patient identification transmitter 14x may be used for tracking the location of the hub 15 separately from the patient.

The location tracking system 40 may further be configured to track the locations of various other individuals and devices within a care facility. Various individuals occupying a care facility may have identification transmitters transmitting an identifier associated to them, or at least to their role in the care facility. In the example of FIG. 1, the system 1 includes at least one clinician identification transmitter 71 incorporated in a clinician device 70, which for example may be a handheld or wearable device. The clinician identification transmitter 71 transmits a clinician identifier 60 (e.g., a nurse identifier, physician identifier, individualized clinician identifier, or the like) via communication link 41e to a respective identification receiver 46a, 46n of the location tracking system 40. In certain examples, each clinician may have an identification transmitter 71 corresponding to their role in patient care, such as nurses carrying nurse location transmitters that transmit a nurse identifier, physicians carrying physician location transmitters that transmit a clinician identifier, etc. Alternatively, each clinician may carry a location transmitter that transmits an identifier associated with and identifying that individual clinician within the location tracking system 40. The role of the clinician is then determined, if needed, based on the identity of the respective clinician. In addition to and separate from clinician resources that tend to move from location to location to perform their role responsibilities, some members of the care team such as Centralized Monitoring Technicians or eICU (electronic Intensive Care Unit) nurses and physicians may perform their responsibilities from a command and control like workstation located in the hospital or at a remote facility and do not tend to move to perform their care delivery support activities (i.e., patient monitoring, alarm notification to care team, ECG waveform interpretation, etc.). In one example, the location tracking system 40 may acquire information about these single location-based resources and associate them to a given patient room from a staffing, assignment, workforce management, etc. system.

In the depicted embodiment, a plurality of identification receivers 46a-46n are placed at known locations throughout a care facility. The identifier transmitted by the respective identification transmitter 14a-14c, 14x, 71 is received by one of the identification receivers 46a-46n closest to, or otherwise arranged to receive transmissions from, identification transmitters 14a-14c, 14x, 71 at that particular location of the tracked individual or device. Each identification receiver 46a-46n then communicates the patient identifier 61 or clinician identifier 60, along with its own receiver identification, to a location tracking module 22. For example, the identification receiver 46a, 46n may communicate the patient identifier 61 and/or clinician identifier 60 and its own identification with a host network 30 for the care facility via a respective communication link 49a, 49n. The location tracking module 22 then monitors and determines a patient location 68 and/or clinician location 66 for the location tracking system 40 within the care facility.

The location tracking module 22 then determines a patient location 68 or clinician location 66 based on which identification receiver 46a-46n receives the identifier for that individual from one or more of the identification transmitters 14a-14c. For example, the location tracking module 22 may access a map or database of the care facility where each identification receiver 46a-46n is associated with a particular location in the care facility. The map associating each identification receiver 46a-46n with a location in the care facility may be, for example, uploaded and stored in the computing system 235 of the host network 30 as part of the system configuration.

The clinician device 70 also includes a user interface display 72 that displays information to the clinician and receives input from the clinician. The user interface display 72 includes any type of display device appropriate for a portable, handheld or wearable device, which may be a touch screen or may include an associated user input means, such as touch and/or voice input means. For example, the user interface display 72 may be utilized to silence or acknowledge an alarm event. Alternatively or additionally, the user interface display 72 may be utilized for a clinician to control an availability mode or clinician availability indicator 64 that indicates that clinician's availability to treat a patient and/or to respond to an alarm condition, or the like.

In certain embodiments, the clinician availability indicator 64 may be used by the incident analysis module 24 alone or in combination with the clinician location 66, to determine whether a subsequent alarm 59b can be part of an incident group 63. For example, the incident analysis module may further determine the termination time $T_t$ of the incident group 63 when the clinician leaves the patient's location 68—e.g., when the clinician location 66 is no longer equal to the patient location 68. Alternatively or additionally, the termination time $T_t$ of the incident group 63 may be based on when the clinician changes their availability indicator 64 to indicate that they are no longer attending to the patient. Likewise, the termination time $T_t$ may be determined based on the last occurring of the aforementioned events relating to the clinician location 66 or clinician availability indicator 64, and/or a predetermined time interval thereafter.

Identification receivers 46 may be provided at fixed locations throughout the care facility, such as at each room, bed, bay, hallway, etc. to enable tracking the patient's location and the clinician's location throughout the care facility. Each patient 4 and their associated wireless monitoring system may be assigned a primary identification receiver 46. For example, the primary identification receiver (e.g., 46a) may be located at the location where the patient is likely to spend the most time, such as the patient's assigned room, bed, bay, etc. For example, each patient room may be equipped with an identification receiver 46 dedicated to that room, which may then be associated to the patient when the patient 4 is assigned to that room. When the respective patient identifier 61 is received by the primary identification receiver 46a, that is indicates that the patient is located in their assigned room. A clinician location 66 can be determined to be equal to the patient's location 68, and thus that the clinician is attending to the patient, when the respective clinician identifier 60 is also received by the primary identification receiver 46a.

In certain embodiments, each patient room may be equipped with multiple identification receivers 46 which may provide detailed information about the patient location 68 and/or clinician location 66 within the room. In such an embodiment, one of the identification receivers 46 may be identified as the primary identification receiver (e.g., 46a) which, for example, may be associated with the patient's bed. In an exemplary scenario, each patient room has two identification receivers 46. The primary identification receiver (e.g., 46a in the example of FIG. 1) receives the patient identifier 61 when the patient is in their bed or in the main part of their room. Other second identification receivers may be located in other portions of the patient's room, such as a bathroom, depending on the level of preciseness of location tracking required or desired.

FIG. 1 provides an exemplary system where the primary identification receiver 46a may be provided in a charger 44 associated with the monitoring system, such as associated with one or more of the sensing devices 3a-3c. As the charger 44 is likely a device that remains plugged in to a power source, such as a wall outlet, the charger 44 is not a portable device and thus remains at a relative fixed location during a monitoring period. For example, the charger 44 may remain plugged in to a wall outlet in a patient's room, or otherwise remain plugged into a particular power source. Thus the charger 44 remains at a relative fixed and known location—e.g., movement of the charger 44 is restricted by the length of the power cord connecting it to the power source. Accordingly, the charger 44 provides a reliable fixed and known location for placement of the identification receiver in a patient's room.

For example, each sensing device 3a-3c may have a battery 7a-7c that is charged by the respective charger 44. The battery 7a-7c may be a removable battery that can be removed from the respective sensing device 3a-3c and placed on the charger 44 for charging, and a replacement battery may be inserted into the respective sensing device 3a-3c. For example, all of the sensing devices 3a-3c may utilize identical batteries 7a-7c, and thus the charger 44 may provide a bank of charging slots where batteries can be swapped and charged as each sensing device requires. Alternatively, the charger 44 may be configured to connect to each respective sensing device 3a-3c in order to charge the respective batteries 7a-7c. Likewise, the charger 44 may be configured to charge a battery 27 of the hub 15.

The patient identification transmitters 14a-14c, 14x communicate with one of a plurality of identification receivers 46a, 46n via a respective communication link 41a-41c, 41x. Likewise, each clinician identification transmitter 71 communicates with one of the plurality of identification receivers 46a, 46n via a respective communication link 41e. The communication link 41a-41c, 41x may be by any of various wireless communication protocols and/or platforms, such as Bluetooth, Bluetooth Low Energy (BLE), ZigBee, Wi-Fi, infrared, ultrasound, or by other wireless communication means. In certain embodiments, it is preferable that the transmission range of the patient identifier be limited so that the patient identification transmitters 14a-14c, 14x are only within communication range of one identification receiver 46a-46n at a time. Thus, it may also be beneficial if the system is configured such that the communication signals and protocols do not pass through walls or other structural barriers so that identification receivers 46a, 46n can be placed in adjacent rooms, such as adjacent hospital rooms, without concern of cross-receiving. Accordingly, infrared may provide a good means for the communication links 41a-41c, 41x in other embodiments where line-of-sight limitations are prohibitive, other relatively short-range protocols may be desirable, such as Bluetooth, Bluetooth Low Energy (BLE), or ZigBee, or the like. Alternatively or additionally, communication between the identification receivers 46a, 46n and the identification transmitters 14, 71 may be via a publish-subscribe messaging pattern, or model.

The identification receiver 46a, 46n may communicate with the host network via a separate receiver/transmitter (e.g., 48) that communicates with a respective receiver/transmitter 34 associated with the host network 30. Alternatively, one or more of the identification receivers 46a-46n may have a transmitter incorporated therein capable of transmitting the patient identifier and its own receiver identifier to a respective receiver/transmitter 34n associated with the host network 30. The patient identifier is communicated to the host network 30 via a respective communication link 49a-49n, which may be by any wireless or wired means and according to any communication protocol. For example, communication may be via a Wi-Fi network for the care facility, or by a dedicated wireless network for the location tracking system 40. For example, in certain embodiments the location tracking system 40 may employ one or more wireless local area networks (WLANs) situated throughout a care facility. In other embodiments, the devices on the location tracking system 40 may utilize the (WMTS) spectrum. Alternatively or additionally, communication between the identification receivers 46a, 46n and the host network 30 may be via a publish-subscribe messaging pattern, or model. In such an embodiment, the identification receivers 46a, 46n may publish information, and the host network 30 may subscribe to the published "messages" from the identification receivers 46a, 46n, or vice versa. Accordingly, the host network 30 does not need to establish a direct communication link with identification receivers 46a, 46n, and vice versa, and each can continue to operate normally regardless of the other.

In the embodiment depicted in FIG. 1, the identification transmitters 14a-14c, 14x, 71 are provided in the sensing devices 3a-3c and/or the hub 15 with the identification receivers 46a-46n provided at fixed and known locations throughout the care facility. A person having ordinary skill in the art will understand in light of this disclosure that, in other embodiments the identification receivers 46a-46n may travel with the tracked patient, clinician, device, etc. (such as provided in the sensing devices 3a-3c and/or the hub 15, and in the clinician device 70), and transmitters may be provided at fixed locations throughout the care facility to transmit a location identifier of that fixed location. In such an embodiment, the respective sensing devices 3a-3c and/or clinician device 70 would receive the location identifier emitted by a location transmitter and would be equipped to determine its own location based on the location identifier received.

Returning to the depicted example, the location tracking module 22 is configured to receive the patient identifier 61 associated with the patient and/or the clinician identifier 60 associated with a respective clinician, as well as the identification of the receiver 46a, 46n that received that patient identifier 61 or clinician identifier 60. Based thereon, the location tracking module 22 determines a patient location within a care facility. For example, the location tracking module 22 may be configured with the map of the care facility, where a location of each identification receiver 46a-46n is associated to a location on the map. Thus, when a patient identifier 61 and/or clinician identifier 60 is received at a particular identification receiver 46a, 46n, the location tracking module 22 determines the patient location 68 for the patient associated with the patient identifier 61 and/or the clinician location 66 associated with the clinician identifier 60 to be a given location range on the map of the care facility associated with the identification receiver 46a, 46n that received the patient identifier. For example, the patient location may be determined to be the patient room associated with the identification receiver 46a assigned to or associated with that room.

As a patient or a clinician moves throughout a care facility, the identifier transmitted by the respective identification transmitters 14a-14c, 14x, 71 are received by different identification receivers 46a, 46n, and the location tracking module 22 may update the patient location 68 or the clinician location 66 as a new identification receiver 46a, 46n reports receiving the respective identifier. Further, the location tracking module 22 may store the patient location 68 and the clinician location 66 in order to track and store the respective locations over time.

The hub device 15 may further include a display 16 and a speaker 18 that may be used to generate an alert or alarm and/or to display information regarding the patient's location, activity, physiological condition, etc. The display 16 may be any type of digitally-controlled visual display, and may further be a touchscreen controllable by a user to provide input to the hub 15, such as to silence an alert or alarm.

The hub device may further include computing system 135 having processor 139 and storage system 141. The hub device 15 may serve to control the sensing devices 3a-3c, and thus may transmit operation commands to the respective sensing devices 3a-3c via the communication link 11a-11c to control their monitoring operations. The hub 15 may contain a monitoring regulation module 23 that is a set of software instructions stored in memory and executable on the processor to assess the physiologic parameter data collected by the sensing devices 3a-3c and determine a patient condition therefrom, such as to detect an alarm event, and to control the respective sensing devices 3a-3c according to the patient condition. For example, the alarm event may be determined by comparing the physiological parameter data collected by one or more of the sensing devices 3a-3c with alarm limits to determine whether the patient condition requires generating an alarm to alert the clinician to the patient's condition.

The incident analysis module 24 may further, in a non-limiting example, determine or calculate an incident severity value 79 (or like factor or factors) for each incident group 63. For example, the severity value 79 may be based on one or more of a duration of the incident group 63 (from the initiation time $T_0$ to the termination time $T_t$), a number of alarm events 58, 59 in the incident group 63, or an alarm type of each alarm event 58, 59 in the incident group 63. Alternatively or additionally, the example incident severity value 79 may be calculated based on the amount of clinician resources utilized to respond to an incident group 63, such as a total amount of clinician time spent related to the incident group 63 and/or a total number of clinicians that responded to an incident group 63. Accordingly, the severity value 79 can provide information regarding how much work was required to respond to a single alarm event or incident group 63, and/or indicate the amount of resources that were required to respond and alleviate the alarm event or incident group 63.

The incident severity value 79 may take any form capable of indicating the relative severity of a particular incident group 63. For example, the incident severity value 79 may be provided on a numerical scale, a color scale, or similar. In one embodiment, the incident severity value 79 may be calculated by allocating weights to the various values for the respective incident groups—e.g., duration, alarm types, alarm level, clinician or collective clinician time spent, number of clinicians, involved clinician(s) skillset levels, device resources, etc.—and locating the resulting value on a scale from least severe (e.g., requiring minimal resources) to most severe (e.g., requiring a significant amount of resources). For example, the number of alarm events 58, 59, alarm types, and alarm levels may be used as indicators of the amount of resources required to respond to the incident group 63. Certain alarm types, such as technical alarm types, may be considered to require minimal resources. For example, in certain situations technical alarm types may receive treatment by dedicated technicians rather than nurses. In such situations technical alarm types may then be associated with minimal resource usage as compared to physiological alarm types. Similarly, alarm level can also indicate an amount of resources utilized to respond to each alarm event 58, 59, and thus the incident group 63 as a whole. For example, each alarm event 58, 59 may include indication of an alarm level, such as based on the alarm limits exceeded and how far the physiological parameter data recorded by the respective sensing device 3a-3c exceeds those alarm limits. Likewise, alarm level may account for a code call, which requires significant resources (both clinician resources and device resources) to respond. Additionally, care team support resources (e.g., time, skillset) such as Centralized Monitoring Technicians or eICU nurses and physicians who may be involved in alarm/alert notification and response, patient monitoring, etc. processes can be envisioned to be included in the incident analysis module 24 and subsequent exemplary severity or resource utilization factors. These resources typically perform their responsibilities from a command and control like workstation located in the hospital or at a remote facility and do not tend to move to perform their care delivery support activities.

In certain embodiments, each possible alarm type and alarm level is allocated a numerical value according to the amount of resources typically required by that respective alarm type and alarm level. In such an embodiment, a numerical value may be calculated as the incident severity value 79, which then can be associated with and indicate the amount of resources required to respond to the respective incident group 63. In the non-limiting example illustrated at FIG. 2, the incident severity value 79 may be a numerical value between one and ten calculated for each incident group 63, where one is the least severe and least resource intensive incident group and ten is the most severe and most resource intensive incident group 63.

In FIG. 2, for example, the incident severity values 79 for each incident group 63a-63e are presented above the respective incident group. Patient 1 experiences a first incident group 63a having an incident severity value 79 equal to a five out of ten (where the incident involves five overlapping alarm incidents 58, 59a, $59b_1$-$59b_3$). The incident severity value 79 for the third incident group 63c for patient 1 is also a level five out of ten, which is based at least in part on the fact that it has a longer duration 77 caused by the spacing of the alarm events 58, 59a, and $59b_1$-$59b_2$. Additionally, the alarm level of the exemplary first alarm event 58 is a high alarm level (indicated in red), which is also accounted for in the severity value 79 determination. The incident group 63b comprising technical alarm events 58, 59a has a low incident severity value 79, equal to one, based on the fact that the technical alarm type is allocated a lesser value and that the alarm events 58, 59a are overlapping such that the duration 77 of the incident group is relatively short. On the other hand, the incident group 63e for patient 3 has a very high incident severity value 79, equal to nine, which is based on the long duration 77 of the incident group 63e, the five alarm events 58, 59a, $59b_1$-$59b_3$, and the fact that the alarm levels of two of the alarm events $59b_1$ and $59b_2$ were severe (indicated in red). Additionally, the incident severity value 79 may be increased based on the amount of clinician resources required, such as if more than one clinician is needed to respond to the incident group 63 or if the clinician was required to treat the patient for longer than the duration 77.

For example, the clinician time usage for each alarm incident may be determined based on the clinician location(s) 66, such as how many clinicians had a clinician location 66 equaling the patient location 68 and how long each clinician spent at the patient location 68. This again can be determined as a numerical value, such as a total amount of clinician time (e.g., in minutes or seconds) is spent at the respective patient location 68. Additionally, such calculation may also account for the type of clinician at the patient location 68. For example, physician time may be weighted heavier than nurse time, and nurse time may be weighted heavier than technician time.

Likewise, clinician time usage may also account for the availability indicator 64 of each clinician whose clinician location 66 pattern indicates that they are attending to the alarm event 58 or incident group 63 for a patient. This can allow tracking of clinician time even as the clinician moves away from the patient location 68, such as to get needed supplies, devices, medication, input orders or information, etc. For example, the clinician device 70 may be configured to automatically set the availability indicator 64 to "unavailable" and link the clinician to the respective patient once the clinician location 66 reaches the patient location 68 during an alarm event 58 or incident group 63. The availability indicator 64 may continue to list the clinician as attending to the alarming patient until the incident group is terminated or the clinician provides input to change the value of the availability indicator 64. Thereby, the clinician time for that clinician may be tracked as the clinician moves about the care facility as needed to attend to the patient.

Figure 5:
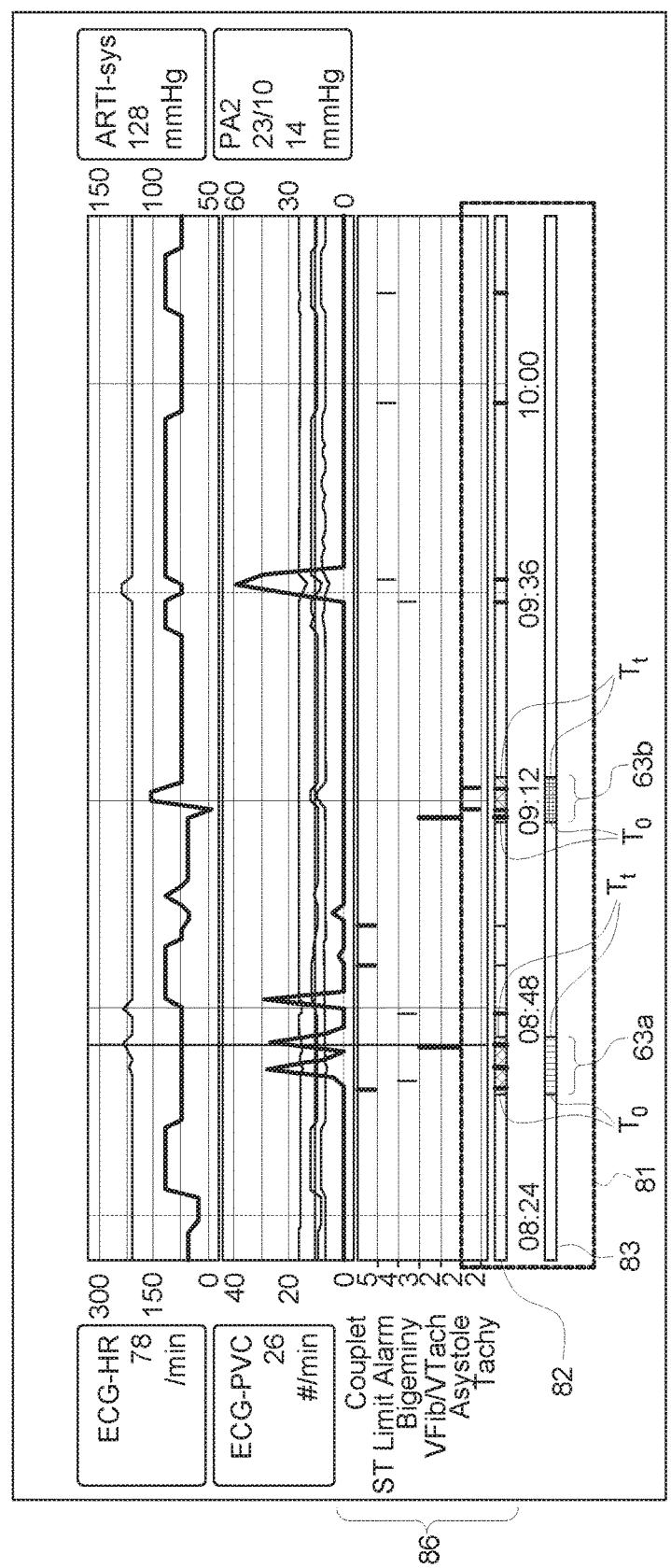
FIG. 5 is an exemplary embodiment of a display providing a visual indicator of multiple incident groups and the severity value of each incident group.

The incident analysis module 24 may further generate a visual indicator to be provided on a display device to visually indicate each incident group 63, such as in conjunction with the display of physiological parameter data recorded by one or more of the sensing devices 3a-3c. The particular configuration of and information provided by the visual indicator may be configurable to provide inclusion or exclusion of different types of incident groups, such as those consisting of particular alarm types that may be of interest. FIG. 5 depicts an exemplary visual indicator 81 where two incident groups 63a and 63b are depicted with respect to time. In the depicted example, the visual indicator 81 is comprised of an incident bar 82 marking all incidents including each alarm event 58, 59 and each incident group 63 that occurred during the depicted time period. An incident group bar 83 is also included in the visual indicator 81 that visually depicts the incident groups 63a and 63b, along with the corresponding incident severity value 79 of each incident group 63a, 63b via color coding. In the example, the first incident group 63a is indicated with a red incident severity value (i.e., red indicating most severe) and the second incident group 63b is depicted with a yellow incident severity value (i.e., yellow indicating medium severity).

Both the incident bar 82 and the incident group bar 83 depict the initiation time $T_0$ and termination time $T_t$ for each incident group 63a, 63b. For example, the visual indicator 81 may be generated based on the information provided in the incident group designator 69 and/or based on the incident severity value 79. The exemplary display shown in FIG. 5 further includes an alarm event panel 86 that depicts each alarm event 58, 59. The incident bar 82 then aggregates all alarm events provided in the alarm event panel 86, as well as each of the incident groups 63a, 63b into a single time-based bar. Thereby, each of the alarm events appearing in each incident group 63a, 63b is depicted by the incident bar 82.

The exemplary display of FIG. 5 may be provided, for example, at a central monitoring station 50, and specifically on a display 52 at the central monitoring station. Alternatively or additionally, the display of FIG. 5 may be shown on the display 16 of the hub 15. At the central monitoring station 50, monitoring information for multiple patients may be displayed at once, such as simultaneously displaying multiple patient-specific displays (e.g., a display like that of FIG. 5 for each patient in the relevant care unit or patient monitoring section provided simultaneously in a grid or an array, or in another arrangement on a large display 52 of a central monitoring station 50).

The incident analysis module 24 is a set of software instructions executed on one or more processors within the patient monitoring system 1. In various embodiments, the incident analysis module 24 may be stored and executed within a computing system 235 of the host network 30. Alternatively or additionally, the incident analysis module 24 may be contained locally within the physiological monitoring system attached to or associated with the patient. For example, the incident analysis module 24 (or a portion thereof) may be stored in and executed by a computing system 135 within the hub 15 and/or in one or more of the sensing devices 3a-3c. Further, in certain embodiments, the incident analysis module 24 may be provided in multiple devices within the system 1, such as to carry out various aspects or steps of the methods described herein. In the embodiment of FIG. 1, the incident analysis module 24 is comprised of instructions contained in and executed by both the computing system 235 of the host network 30 and the computing system 135 of the hub 15. Specifically, incident analysis module portion 24a is stored within the storage system 221 of the computing system 235, and incident analysis module portion 24b is stored within the storage system 141 of the computing system 135. Together, the incident analysis module portions 24a, 24b execute instructions to determine the patient location indicator 54 based on the patient location in the care facility and/or other considerations, as described herein. In other embodiments, the incident analysis module 24 may be entirely contained in either the computing system 235 of the host network 30 or the computing system 135 of the hub 15.

In certain examples, communication between the host network 30 to the hub 15 may be via a publish-subscribe messaging pattern, or model. In such an embodiment, the host network 30 may publish information, and the hub 15 and/or the clinician device 70 subscribe to the published "messages" from the location tracking module 22 and/or the incident analysis module 24, or vice versa. Accordingly, the host network 30 does not need to establish a direct communication link with the hub 15 or the clinician device 70, and vice versa, and each can continue to operate normally regardless of the other.

FIG. 4 schematically depicts one embodiment of computing system 235 of the host network 30. The exemplary computing system 235 includes the incident analysis module 24 the location tracking module 22 for determining the clinician location 66 and the patient location 68. The central monitoring module 25 may cooperate with the incident analysis module 24 to display the visual indicator 81 on one or more displays 52 associated with the central monitoring station 50. The computing system 235 generally includes a processing system 219, storage system 221, software 237, and a communication interface 239. The processing system 219 loads and executes software 237 from the storage system 221, including the location tracking module 22, the incident analysis module 24, and the central monitoring module 25, which are applications within the software 237. Each of the modules 22, 24, 25 include computer-readable instructions that, when executed by the computing system 235 (including the processing system 219), direct the processing system 219 to operate as described in herein in further detail, including to execute the steps to identify an incident group 63 and generate and store an incident group designator 69.

Although the computing system 235 as depicted in FIG. 4 includes one software 237 encapsulating one location tracking module 22, the incident analysis module 24, and one central monitoring module 25, it should be understood that one or more software elements having one or more modules may provide the same operation. For example, the modules 22, 24, 25 may be combined into a shared set of instructions carrying out the steps described herein, or may be divided into any number of modules, which may be stored on separate storage devices and executed by different processing systems. Similarly, while description as provided herein refers to a computing system 235 and a processing system 219, it is to be recognized that implementations of such systems can be performed using one or more processors, which may be communicatively connected, and such implementations are considered to be within the scope of the description. For example, the computing system 235 may represent a cloud computing system and application implemented across multiple networked processing and storage devices.

The processing system 219 may include any one or more processing devices, such as one or more microprocessors, general purpose central processing units, application-specific processors, microcontrollers, or any other type of logic-based devices. The processing system 219 may also include circuitry that retrieves and executes software 237 from storage system 221. Processing system 219 can be implemented within a single processing device but can also be distributed across multiple processing devices or subsystems that cooperate in executing program instructions, such as in the cloud-computing application described above.

The storage system 221, which includes the patient medical record database 33, can comprise any storage media, or group of storage media, readable by processing system 219, and capable of storing software 237. The storage system 221 can include volatile and non-volatile, removable and non-removable media implemented in any method or technology for storage of information, such as computer-readable instructions, data structures, program modules, or other data. Storage system 221 can be implemented as a single storage device but may also be implemented across multiple storage devices or sub-systems. For example, the software 237 may be stored on a separate storage device than the medical record database 33. Likewise, medical record database 33 can be stored, distributed, and/or implemented across one or more storage media or group of storage medias. Similarly, medical record database 33 may encompass multiple different sub-databases at different storage locations and/or containing different information which may be stored in different formats. Storage system 221 can further include additional elements, such a controller capable of communicating with the processing system 219.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 219, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 239 interfaces between the elements within the computing system 235 and external devices, such as various receiver/transmitters 31, 34a-34n that receive and transmit information to and from the host network 30. For example, the communication interface may operate to receive patient identifiers 61, clinician identifiers 60, and the corresponding receiver identifications 62 (providing the identification receiver 46a, 46n that received the patient/clinician identifier(s) generated via the location tracking system 40, receive alarm events 58, 59 from the hub 15 and/or directly from one or more of the sensing devices 3a-3c. The communication interface may further display of the visual indicator 81 such as at the central monitoring station 50.

Figure 6:
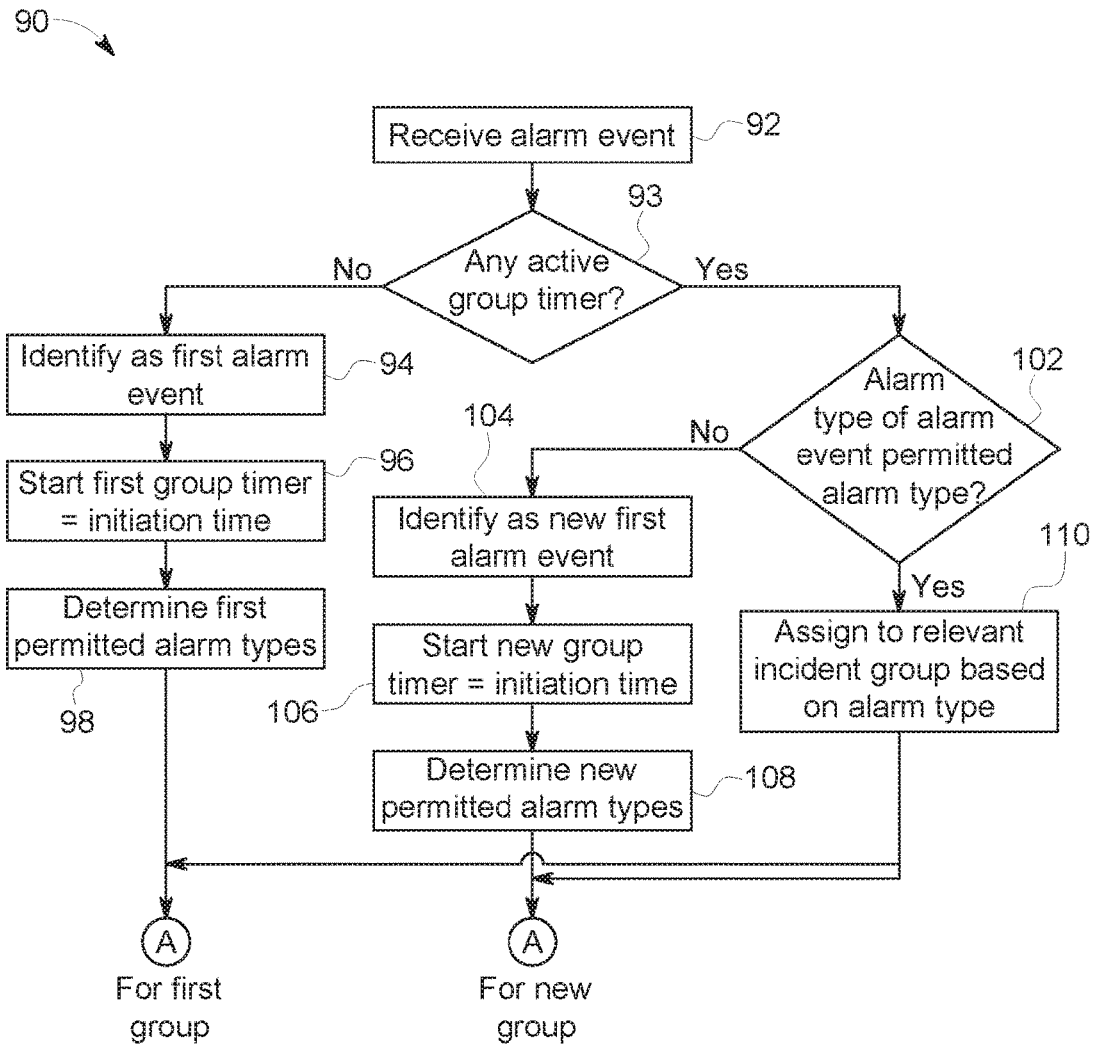
FIGS. 6-8 depict embodiments of patient monitoring methods, or portions thereof, providing incident grouping of alarm events.
Figure 7:
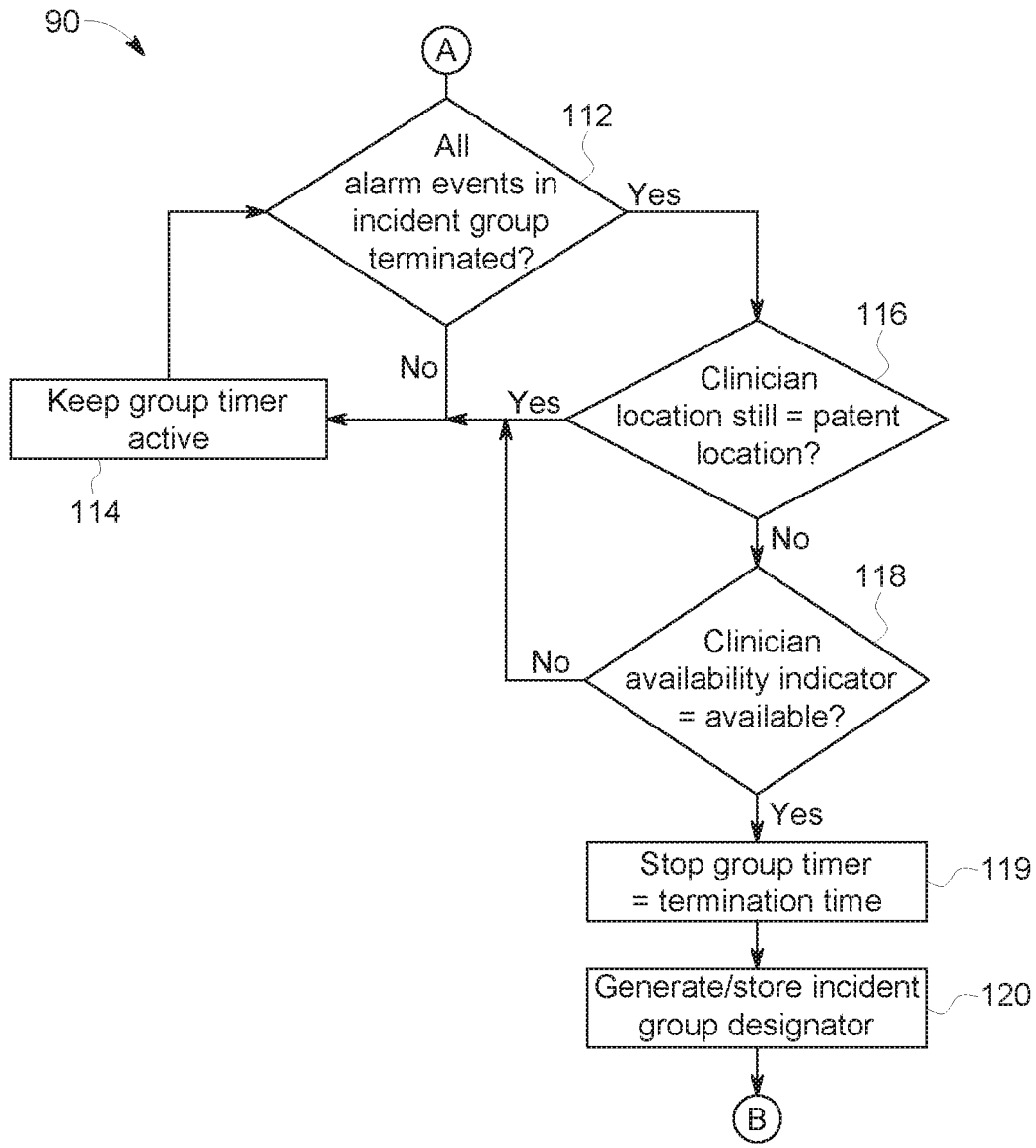
Figure 8:
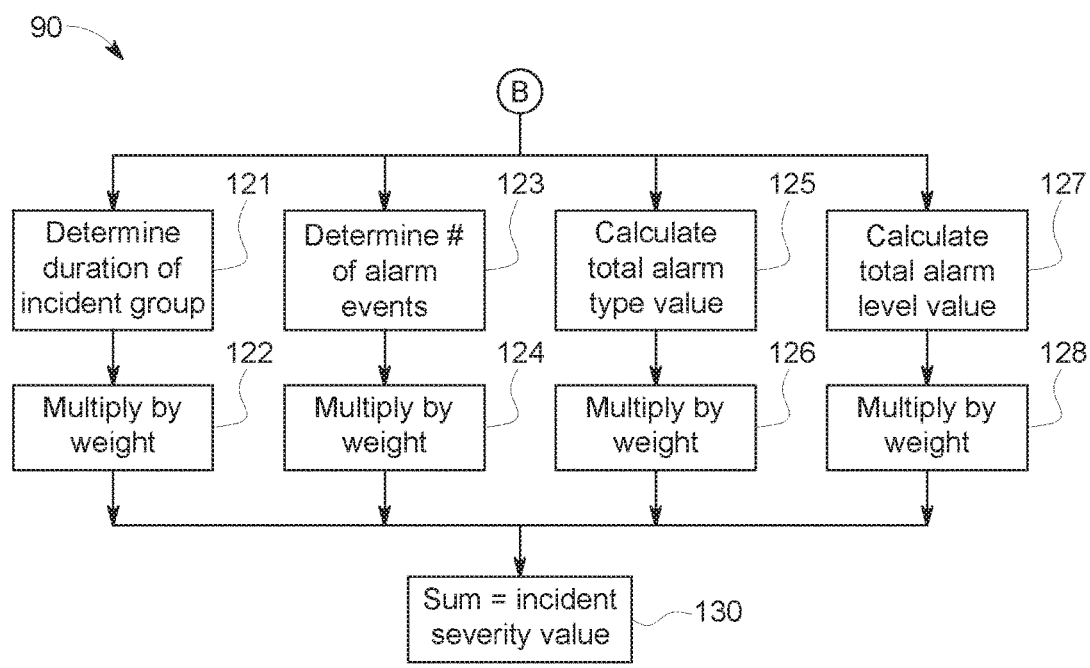

FIGS. 6-8 depict exemplary embodiments of various portions of a method 90 of monitoring a patient involving incident group identification. FIGS. 6 and 7 depict an exemplary embodiment of steps executed for incident identification. Starting at FIG. 6, an alarm event is received at step 92. Step 93 determines whether any group timer is currently active. If not, then the received alarm event is identified as a first alarm event at step 94 and a first group timer is started at step 96 based on an initiation time of the received alarm event. One or more first permitted alarm types are determined at step 98 based on the alarm type of the first alarm event. The method then continues to execute the steps depicted at FIG. 7 to monitor and control the first group timer according to the steps depicted at FIG. 7. As will be understood in view of the disclosure, the depicted method steps are recursive so that any number of alarm events meeting the depicted criterion and rules can be included in an incident group.

Returning to step 93, if any group timer is already active, then steps are executed at step 102 to determine whether an alarm type of the alarm event is a permitted alarm type (which may be one of the first permitted alarm types or one of a new set of permitted alarm types). If the alarm type is not on any list of permitted alarm types, then the received alarm event is identified as a new first alarm event at step 104. A new group timer is started at step 106 based on the initiation time of the received alarm event, and new permitted alarm types are determined at step 108. The steps depicted in FIG. 7 are then executed to monitor and control the new group alarm timer.

Returning to step 102, if the alarm type of the received alarm event is a permitted alarm type, then steps are executed at step 110 to assign the received alarm event to the relevant group based on the alarm type. For example, the received alarm may be assigned to the first incident group associated with the first alarm event created at step 94, or to the incident group associated with the new first alarm event created at step 104. Numerous incident group analyses may continue simultaneously and each will have its own timer for which the control logic exemplified at FIG. 7 is executed.

Step 112 is executed to determine whether all alarm events in the respective incident group have been terminated. If any alarm events are active, then the respective group timer remains active at step 114. If all alarm events in the respective incident group have been terminated, then step 116 is executed to determine whether the clinician is still at the patient location (e.g., whether the clinician location 66 equals the patient location 68 as provided by the location tracking system 40). If the clinician is still at the patient location, then it is assumed that the clinician is still tending to matters related to alarm events in the incident group, and thus the group timer remains active at step 114. If the clinician has left the patient location, logic may be executed at step 118 to determine whether the clinician availability indicator 64 indicates that the clinician is unavailable and tending to matters relating to the alarm events in the incident group. If the clinician remains unavailable then the group timer remains active at step 114. Once the clinician becomes available, then the respective group timer is stopped at step 119 establishing the termination time. Steps are then executed at step 120 to generate and store the incident group designator, which includes information regarding the initiation time and termination time of the incident group and the alarm events comprising the incident group. In other embodiments, especially where the analysis of the alarm events is being conducted post-hoc, the timer may be eliminated and the analysis may only involve location of the initiation time and termination time of each alarm incident.

For each incident, which may comprise an incident group or a single alarm event, steps are executed to determine the incident severity value 79. One exemplary method of determining the incident severity value is exemplified at FIG. 8, where incident severity is calculated based on the duration of the incident, the number of alarm events in the incident, the total alarm type value for the incident, and the total alarm value (e.g., based on an alarm severity indicator). These values are exemplary, and in other embodiments the incident severity may be calculated based on other values, such as the number of clinicians involved in responding to the alarm incident and/or other quantitative or qualitative assessments of resource utilization. Similarly, the incident severity value determination may be a subset of these exemplary values, alone or in combination with other values. Accordingly, the incident severity value may be used to indicate or assess resource utilization from a qualitative standpoint, such as how taxing or stressful the particular alarm incident or other event may have been to the clinician.

In the example of FIG. 8, a duration of the incident group is determined at step 121 and is multiplied by a predetermined weight at step 122. A number of alarm events in the incident group is determined at step 123 and is multiplied by a predetermined weight at step 124. A total alarm type value is calculated at step 125 and is multiplied by a predetermined weight at step 126. The total alarm type value is calculated or determined based on the alarm types of the alarm events in the respective incident group. For example, the total alarm type value may be a sum of all the alarm type values of the alarm events in the incident group. Alternatively, the total alarm type value may be an average of the alarm types, the median of the alarm types, a maximum of all of the alarm type values, or any other calculated value based on the alarm types in the incident group. A total alarm level value is calculated at step 127 and then multiplied by a respective predetermined weight at step 128. The total alarm level value may be the sum of all alarm level values for the alarm events in the incident group, or calculated based on the respective alarm level values as previously described. The weight values may be configurable, such as by a system administrator or by an attending clinician, as the various quantities may have different significances to the total resources required in various clinical or hospital settings. Step 130 is then executed to sum all of the calculated values in order to reach the incident severity value. The incident severity value may be stored along with the incident group designator. For example, the incident group designator and/or severity value may be stored in the patient's medical record along with the physiological parameter data and/or any alarm event information.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A computer-implemented method of monitoring a patient, the method comprising:
    recording physiological parameter data from the patient with a sensor device;
    with a processor:
        detecting a first alarm event;
        activating a group alarm timer based on an initiation time of the first alarm event;
        detecting one or more subsequent alarm events while the group alarm timer is active;
        for each detected subsequent alarm event, determining whether the respective subsequent alarm event is part of an incident group with the first alarm event;
        stopping the group alarm timer at a termination time based on termination of all alarm events in the incident group;
        wherein the termination time is further based at least one of a clinician location or a clinician availability indicator; and
        generating an incident group designator identifying the incident group.

2. The method of claim 1, wherein the termination time is upon termination of all alarm events in the incident group.

3. The method of claim 1, wherein the termination time is after a predetermined time interval following termination of all alarm events in the incident group.

4. The method of claim 3, wherein termination of all alarm events is when all alarm events in the incident group have been silenced by a clinician.

5. The method of claim 3, wherein termination of all alarm events is when a triggering basis for each alarm event in the incident group is no longer present.

6. The method of claim 1, wherein determining that the subsequent alarm event is part of the incident group includes identifying one or more permitted alarm types based on a first alarm type of the first alarm event, and determining that a subsequent alarm type of each subsequent alarm is among the one or more permitted alarm types.

7. The method of claim 6, wherein determining that the subsequent alarm event is part of the incident group includes determining that neither the first alarm type nor the subsequent alarm type is a technical alarm type, or determining that both the first alarm type and the subsequent alarm type is the technical alarm type.

8. The method of claim 1, further comprising:
    determining that one of the subsequent alarm events is not part of the incident group with the first alarm event;
    activating a new group alarm timer based on a new initiation time of the respective subsequent alarm event that is not in part of the incident group with the first alarm event;
    for each detected subsequent alarm event that is not part of the incident group with the first alarm event, determining whether the respective subsequent alarm event is part of a new incident group with the respective subsequent alarm event that is not in part of the incident group.

9. The method of claim 1, further comprising calculating an incident severity value for the incident group based on one or more of a duration of the incident group, a number of alarm events in the incident group, an alarm type of one or more of the first alarm event and the subsequent alarm events, and an alarm level of one or more of the first alarm event and the subsequent alarm events.

10. The method of claim 9, wherein the incident severity value is calculated further based on at least one of a clinician location, a total clinician time spent related to the incident group, and a total number of clinicians detected at a patient location during the incident group.

11. The method of claim 1, further comprising displaying on a display device a visual indicator of the incident group, including the initiation time and the termination time of the incident group with respect to the first alarm event and the subsequent alarm events.

12. A patient monitoring system comprising:
    one or more sensor devices that record physiological parameter data from a patient;
    a processor;
    a location system that determines a clinician location;
    an incident analysis module executable on the processor to:
        receive a first alarm event;
        receive a second alarm event;
        determine that the second alarm event is part of an incident group with the first alarm event;
        receive one or more subsequent alarm events while at least one of the first alarm event or the second alarm event is occurring or within a predetermined time after termination of the first alarm event or the second alarm event;
        for each detected subsequent alarm event, determine whether the respective subsequent alarm event is part of an incident group with the first alarm event;
        receive the clinician location and determine a termination time of the incident group based on the clinician location; and
        generate an incident group designator identifying the incident group.

13. The patient monitoring system of claim 12, wherein the incident analysis module is further executable to:
    activate a group alarm timer based on an initiation time of a first alarm event and stop the group alarm timer at the termination time based further on termination of all alarm events in the incident group;
    wherein each subsequent alarm event that is part of the incident group is received while the group alarm timer is active.

14. The patient monitoring system of claim 12, wherein the termination time is determined as a predetermined time interval after the clinician location indicates that a clinician has left a patient location.

15. The patient monitoring system of claim 12, wherein determining that the subsequent alarm event is part of the incident group includes identifying one or more permitted alarm types based on a first alarm type of the first alarm event, and determining that a subsequent alarm type of each subsequent alarm is among the one or more permitted alarm types.

16. The patient monitoring system of claim 12, wherein the incident analysis module is further executable to generate a visual indicator of the incident group, including an initiation time and the termination time of the incident group with respect to the first alarm event and the subsequent alarm events.

17. The patient monitoring system of claim 12, wherein the incident analysis module is further executable to calculate an incident severity value for the incident group based on one or more of a duration of the incident group, a number of alarm events in the incident group, an alarm type of one or more of the first alarm event and the subsequent alarm events, and an alarm level of one or more of the first alarm event and the subsequent alarm events.

18. The patient monitoring system of claim 17, wherein the incident analysis module is further executable to generate a visual indicator of the incident group depicting the duration of the incident group and the severity value of the incident group.

19. The method of claim 1, wherein the termination time is determined as a predetermined time interval after the clinician location indicates that a clinician has left a patient location.

\* \* \* \* \*